(12) United States Patent
Sherman et al.

(10) Patent No.: US 9,663,421 B2
(45) Date of Patent: May 30, 2017

(54) COUPLING OF LIGHT ALKANES TO LIQUID FUELS

(71) Applicant: Reaction 35, LLC, Houston, TX (US)

(72) Inventors: Jeffrey H. Sherman, Vero Beach, FL (US); Peter Stoimenov, Santa Barbara, CA (US)

(73) Assignee: REACTION35, LLC, Houston, TX (US)

( * ) Notice: Subject to any disclaimer, the term of this patent is extended or adjusted under 35 U.S.C. 154(b) by 326 days.

(21) Appl. No.: 14/313,596

(22) Filed: Jun. 24, 2014

(65) Prior Publication Data

US 2014/0378719 A1  Dec. 25, 2014

Related U.S. Application Data

(60) Provisional application No. 61/838,711, filed on Jun. 24, 2013.

(51) Int. Cl.

| | |
|---|---|
| *C07C 2/86* | (2006.01) |
| *C07C 5/03* | (2006.01) |
| *C07C 1/26* | (2006.01) |
| *C07C 1/30* | (2006.01) |
| *C07C 17/10* | (2006.01) |
| *C07C 17/269* | (2006.01) |

(52) U.S. Cl.
CPC ............... *C07C 2/861* (2013.01); *C07C 1/26* (2013.01); *C07C 1/30* (2013.01); *C07C 5/03* (2013.01); *C07C 17/10* (2013.01); *C07C 17/269* (2013.01)

(58) Field of Classification Search
CPC .. C07C 1/26; C07C 1/30; C07C 2/861; C07C 5/03
See application file for complete search history.

(56) References Cited

U.S. PATENT DOCUMENTS

| 3,855,347 A * | 12/1974 | Oricchio | ................ B01J 23/40 208/262.1 |
|---|---|---|---|
| 7,883,568 B2 | 2/2011 | Gadewar et al. | |
| 2005/0171393 A1 | 8/2005 | Lorkovic | |
| 2005/0234276 A1 | 10/2005 | Waycuilis | |

(Continued)

OTHER PUBLICATIONS

International Search Report and Written Opinion issued in International Application No. PCT/US2014/043887, dated Oct. 20, 2014 (9 pages).

(Continued)

*Primary Examiner* — Sharon Pregler
*Assistant Examiner* — Alyssa L Cepluch
(74) *Attorney, Agent, or Firm* — Adolph Locklar (57) ABSTRACT

A method can include reacting a stream including one or more $C_3$ to $C_{10}$ alkanes with bromine in a bromination reactor to form a bromination reactor discharge stream that includes alkylbromides and HBr. The method further includes coupling the alkylbromides in a coupling reactor to form a coupling reactor effluent comprising alkylbromides having between 5 and about 1000 carbon atoms, olefins having between 5 and about 1000 carbon atoms and HBr. The method also includes hydrogenating the alkylbromides having between 5 and about 1000 carbon atoms and olefins having between 5 and about 1000 carbon atoms to form alkanes having between 5 and about 1000 carbon atoms and HBr.

18 Claims, 3 Drawing Sheets

(56) References Cited

U.S. PATENT DOCUMENTS

| | | |
|---|---|---|
| 2007/0043248 A1* | 2/2007 | Wu .......................... C07C 5/05 585/521 |
| 2008/0269534 A1 | 10/2008 | Lorkovic et al. |
| 2009/0005620 A1 | 1/2009 | Waycuilis et al. |
| 2010/0121119 A1 | 5/2010 | Sherman et al. |
| 2011/0218375 A1 | 9/2011 | Lorkovic |
| 2012/0009090 A1 | 1/2012 | Gadewar et al. |
| 2012/0053381 A1 | 3/2012 | Evans et al. |
| 2013/0006024 A1 | 1/2013 | Kurukchi et al. |
| 2013/0078157 A1 | 3/2013 | Stoimenov et al. |
| 2013/0158324 A1 | 6/2013 | Waycuilis et al. |

OTHER PUBLICATIONS

Zhang et al., "Improved light olefin yield from methyl bromide coupling over modified SAPO-34 molecular sieves"; Phys. Chem. Chem. Phys., vol. 13, pp. 2250-2555 (2011).

Ding et al., "Hydrodebromination and Oligomerization of Dibromomethane"; ACS Catal. vol. 2; pp. 479-486; Feb. 28, 2012.

* cited by examiner

COUPLING OF LIGHT ALKANES TO LIQUID FUELS

CROSS-REFERENCE TO RELATED APPLICATIONS

This application is a non-provisional application which claims priority from U.S. provisional application No. 61/838,711, filed Jun. 24, 2013.

FIELD

The present disclosure generally relates to the formation of heavier alkanes from lighter alkanes.

BACKGROUND

Alkanes having between 3 and 10 carbons ("$C_3$ to $C_{10}$ alkanes"), including alkanes such as propane, butane and pentane, are typically found in natural gas and petroleum reservoirs and are often produced as byproducts in refineries and petrochemical plants. Because $C_3$ to $C_{10}$ alkanes may be difficult to transport in methane pipelines, the $C_3$ to $C_{10}$ alkanes may be separated from methane at a gas processing facility so as to render the natural gas suitable for gas pipeline transportation. Operators may desire to recover the $C_3$ to $C_{10}$ alkanes.

BRIEF DESCRIPTION OF THE DRAWINGS

The present disclosure is best understood from the detailed description when read with the accompanying figures. In accordance with the standard practice in the industry, various features are not drawn to scale.

SUMMARY

In an embodiment, a method is disclosed. The method includes reacting a stream including one or more $C_3$ to $C_{10}$ alkanes with bromine in a bromination reactor to form a bromination reactor discharge stream that includes alkylbromides and HBr. The method further includes coupling the alkylbromides in a coupling reactor to form a coupling reactor effluent comprising alkylbromides having between 5 and about 1000 carbon atoms, olefins having between 5 and about 1000 carbon atoms and HBr. The method also includes hydrogenating the alkylbromides having between 5 and about 1000 carbon atoms and olefins having between 5 and about 1000 carbon atoms to form alkanes having between 5 and about 1000 carbon atoms and HBr.

In another embodiment, a method is disclosed. The method includes reacting ethane with bromine in an ethane bromination reactor to form an ethane bromination reactor discharge including monobromoethane, polybromoethane, HBr and ethane. The method also includes separating the ethane bromination reactor discharge to form a monobromoethane stream, a polybromoethane stream, an ethane bromination HBr stream, and an unreacted ethane stream. The method further includes recycling the unreacted ethane stream to the bromination reactor. In addition, the method includes reacting a stream comprising one or more $C_3$ to $C_{10}$ alkanes with bromine in a bromination reactor to form a bromination reactor discharge stream that includes alkylbromides, unreacted $C_3$ to $C_{10}$ alkanes and HBr. The method further includes separating the bromination reactor discharge stream in a monobromoalkyl recovery system into a light hydrocarbons stream including the unreacted $C_3$ to $C_{10}$ alkanes, a monoalkylbromide recovery HBr stream including HBr, an alkane polybromides stream including polybromoalkanes, and a monobromoalkanes stream that includes monobromoalkanes. The method also includes combining the monobromoethane stream with the monobromoalkanes stream and combining the polybromoethane stream with the alkane polybromides stream. The method further includes hydrogenating the polybromoalkanes in the alkane polybromides stream to form a polybromide reactor HBr stream that includes HBr, and a monoalkylbromide recycle stream that includes monobromoalkanes, wherein the monoalkylbromide recycle stream is recycled to the monobromoalkyl recovery system. In addition, the method includes feeding the monobromoalkanes stream to a coupling reactor. Further, the method includes coupling the monbromoalkanes in the coupling reactor to form a coupling reactor effluent comprising alkylbromides having between 5 and about 1000 carbon atoms, olefins having between 5 and about 1000 carbon atoms and HBr. Also, the method includes hydrogenating the alkylbromides having between 5 and about 1000 carbon atoms and olefins having between 5 and about 1000 carbon atoms to form alkanes having between 5 and about 1000 carbon atoms and HBr.

DETAILED DESCRIPTION

The following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed.

A "monobromoalkane" is an alkane having one bromine atom substitution.

A "polybromoalkane" is an alkane having more than one bromine atom substitution.

"Alkyl bromides" include both monobromoalkanes and polybromoalkanes.

Figure 1:
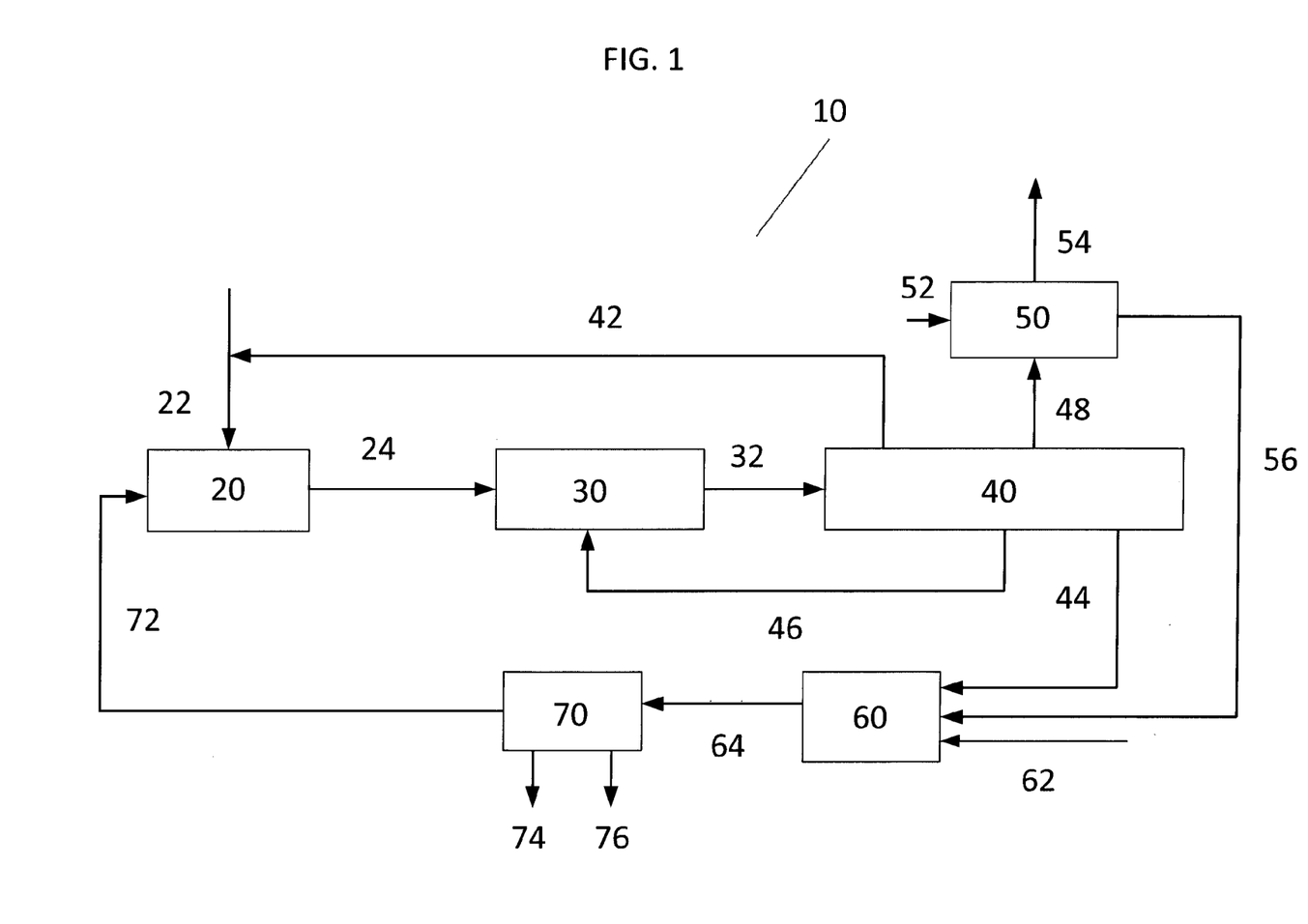
FIG. 1 is a process flow diagram depicting an alkane coupling system consistent with at least one embodiment of the present disclosure.

FIG. 1 is a process flow diagram depicting coupling system 10 consistent with certain embodiments of the present disclosure. Coupling system 10 includes bromination reactor 20, coupling reactor 30, separation system 40, hydrogenation reactor 50, HBR oxidation system 60, and bromine recovery system 70. In bromination reactor 20, reactants from bromination reactor input stream 22 are reacted with bromine ($Br_2$) from dry bromine stream 72 in a bromination reaction to produce bromination reaction products. In certain embodiments, the reactants in the bromination reactor input stream 22 are hereinafter referred to as "bromination reactor reactants." In certain embodiments, the bromine in dry bromine stream 72 and the bromination reactor reactants in bromination reactor input stream 22 may be mixed to form a combined feed stream to bromination reactor 20. In other embodiments, the bromine and bromination reactor reactants may be introduced to bromination reactor 20 separately. The bromination reactor reactants in bromination reactor input stream 22 may be alkanes having between 3 and 10 carbon atoms (referred to as $C_3$ to $C_{10}$ alkanes based on the number of carbon atoms in the alkane). In other embodiments, bromination reactor reactants may be $C_3$ to $C_5$ alkanes. The bromination reactor reactants may include some or all of the isomers of the alkanes. In certain embodiments, bromination reactor input stream 22 includes less than 1% methane, less than 0.5% methane, or less than 0.1% methane (all percentages by weight of total bromination reactor reactants). In some embodiments, bromination reactor input stream 22 includes less than 2% ethane, less than 1% ethane or less than 0.5% ethane (all percentages by weight of total bromination reactor reactants).

Bromination reaction products may include monobromoalkanes, HBr, and polybromoalkanes. In some embodiments, the monobromoalkanes and polybromoalkanes of the bromination reaction products are single and multi-brominated species of the bromination reactor reactants, i.e., propane reacts to become monobromopropane and polybrominated propane, butane reacts to become monobromobutane and polybrominated butane, etc. In certain embodiments of the present disclosure, the bromination reaction is not catalyzed, i.e., the reaction is only thermally induced. Thermal induction means bringing the reactants to an initiation temperature. In other embodiments, the reaction may be catalyzed. At higher temperatures, coke may also be formed in bromination reactor 20.

Reaction conditions for the bromination reaction may be selected to maximize the monobromoalkane yield, minimize formation of polybromoalkanes, or ensure complete conversion of bromine. In certain embodiments, the bromination reaction occurs at temperatures above 200° C. Above 450° C., the bromination reaction may produce unacceptable levels of coke. In certain embodiments of the present disclosure, the bromination reaction may occur between 200° C. and 450° C. In certain embodiments of the present disclosure, the temperature in bromination reactor 20 is between 200° C. and 375° C.

The reaction products of the bromination reaction together with unreacted bromination reactor reactants are discharged from bromination reactor 20 through bromination reactor discharge stream 24. In certain embodiments of the present disclosure, the temperature of bromination reactor discharge stream 24 may be between 250° C. and 350° C. to achieve a desired conversion of bromine. The desired conversion of bromine may be greater than 99%, greater than 99.5% or greater than 99.9%. A more complete conversion of bromine in bromination reactor 20 may allow for the use of less expensive materials of construction downstream of bromination reactor 20.

Because the bromine reaction is exothermic, bromination reactor 20 may be cooled to maintain the bromination reaction within the desired temperature range. In certain embodiments, the bromination reaction is carried out in a shell and tube reactor in which a mixed bromination reactor reactants and bromine feed is introduced into bromination reactor 20 at a temperature greater than or equal to 200° C. The bromination reaction may be carried out inside the tubes, and steam may then be generated on the shell side in order to limit the maximum temperature of bromination reactor 20 to the desired temperature range, such as 250° C.-350° C. The generated steam may be used elsewhere in the process.

In certain embodiments of the present disclosure, a stoichiometric excess of the bromination reactor reactants may be used to increase selectivity to monobromoalkanes and/or to limit temperature rise. In other embodiments of the present disclosure, the bromination reaction is carried out in one or more adiabatic reactors with cooling between the different reactors. This cooling may be achieved using heat exchanger(s) or cold (~35° C.) bromine or bromination reactor reactants. In certain other embodiments of this disclosure, cold (~35° C.) bromine is introduced at multiple positions along the length of bromination reactor 20 to keep the bromination reaction temperature within the desired range. In certain embodiments, this reaction is carried out at higher than atmospheric pressure. In certain other embodiments, this pressure is near that required for subsequent downstream separations. This may significantly improve the efficiency of the entire process by reducing, or preferably eliminating, any required downstream compression prior to separation. In still other embodiments, the bromination reactor may be divided into a cooled section and an adiabatic section.

Bromination reactor discharge stream 24 may be fed to coupling reactor 30, where the bromination reaction products are contacted with a zeolite catalyst at a pressure, temperature and residence time sufficient to cause coupling of the alkyl bromides to form coupling products, including olefins, alkylbromides, alkanes, and HBr. During the coupling reaction, the alkylbromides in the bromination reactor products are coupled to form olefins, akylbromides and alkanes having a greater number of carbon atoms than the alkylbromides in the bromination reactor products. The olefins, alkylbromides and alkanes formed by the coupling reaction may have between 5 and about 1000 carbon atoms. In certain embodiments of the present disclosure, the coupling reaction may be catalyzed. Non-limiting examples of coupling catalysts include non-crystalline alumino silicates (amorphous solid acids), tungsten/zirconia super acids, sulfated zirconia, zeolites, such as SAPO-34 and its framework-substituted analogues (substituted with, e.g., Ni or Mn), ZSM-5 and its ion-exchanged analogs, and framework substituted ZSM-5 (substituted with Ti, Fe, Ti+Fe, B, or Ga). A specific non-limiting example of a coupling catalyst is ion-exchanged ZSM-5 having a $SiO_2/Al_2O_3$ ratio below about 300, below about 100, or about 30 or less. Non-limiting examples of exchanged ions include ions of Ag, Ba, Bi, Ca, Fe, Li, Mg, Sr, K, Na, Rb, Mn, Co, Ni, Cu, Ru, Pb, Pd, Pt, and Ce. The exchanged ions may be exchanged as pure salts or as mixtures of salts. The preparation of doped zeolites and their use as carbon-carbon coupling catalysts is described in Patent Publication No. US 2005/0171393 A1, which is incorporated by reference herein in its entirety. In some embodiments, a fluorinated alumina based solid reactant, as described in more detail below, may be used as the catalyst or as a support for a catalytic material useful in the formation of higher hydrocarbon products. Use of a fluorinated alumina may allow for the simultaneous formation of higher hydrocarbons and capture of hydrogen halide formed in the reaction.

In one embodiment, a Mn-exchanged ZSM-5 zeolite having a $SiO_2/Al_2O_3$ ratio of 30 is used as the coupling catalyst. In another embodiment, a reduced aluminum content zeolite, such as a ZSM-5 zeolite, may be used as the coupling catalyst. In certain embodiments, use of a dealuminated zeolite may result in hydrocarbons with a higher amount of paraffins than a zeolite of the same type that has not been dealuminated. Dealumination of a zeolite catalyst may be accomplished by selective treatment of the hydrogen-exchanged zeolite with a compound that specifically reacts with aluminum centers by forming either volatile compounds at high temperature or soluble complexes when treated in an aqueous solution. Examples of dealumination agents may include mineral acids, such as hydrochloric acid (HCl), hydrofluoric acid (HF), ethylenediaminetetraacetic acid (EDTA), oxalic acid, malonic acid; overheated water steam (steaming); and exchange reagents ($SiCl_4$, $NH_4[SiF_6]$, $NH_4HF_2$, $AlF_3$, trialkyl phosphates, organic phosphites).

Coupling reactor 30 may be a fixed bed, fluidized bed, or other suitable reactor. Coupling reactor 30 may operate at a suitable temperature, such as between 180-300° C. or between 225-275° C.; pressure, such as between 2-100 atmospheres or between 15-50 atmospheres; and residence time ($\tau$) such as between about 1 second to about 45 seconds. Longer residence time may favor conversion of reactants to products, as well as product selectivity, while shorter residence times may result in higher throughput.

The coupling reaction products, unreacted bromination reactor reactants, HBr, and unreacted alkylbromides (collectively, "coupling reactor discharge mixture") may be discharged from coupling reactor 30 through coupling reactor effluent 32. Coupling reactor effluent 32 may subsequently be sent to separation system 40. In separation system 40, the coupling reactor discharge mixture may be separated via distillation and/or absorption/stripping. In certain embodiments, such as shown in FIG. 1, separation system 40 may separate coupling reactor effluent 32 into a light hydrocarbon stream 42, separation system HBr stream 44, which includes HBr, coupling recycle stream 46, and coupled products stream 48. Separation system 40 may be adapted to separate hydrocarbons and alkylbromides having less than a desired number of carbon atoms from those with at least the desired number of carbons. In non-limiting embodiments, the desired number of carbon atoms may be at least 8 carbons, at least 10 carbons, at least 12 carbons, at least 16 carbons or at least 20 carbons. As one of ordinary skill in the art will recognize, the desired number of carbon atoms may be determined by the operator. Light hydrocarbon stream 42 may include alkanes and olefins having less than the desired number of carbon atoms. Light hydrocarbon stream 42 may be recycled to bromination reactor 20 for subsequent bromination. Coupling recycle stream 46 may include alkyl bromides having less than the desired number of carbon atoms. Coupling recycle stream 46 may be sent to coupling reactor 30 for coupling. Coupled products stream 48 may include olefins, alkyl bromides and alkanes having at least the desired number of carbon atoms.

Coupled products stream 48 is hydrogenated with $H_2$ stream 52 in hydrogenation reactor 50. The hydrogenation of the olefins, alkyl bromides and alkanes in hydrogenation reactor 50 may be catalyzed. Non-limiting examples of hydrogenation catalysts include Pd, Pt, Ni, Ru, and Cu. The hydrogenation of the alkyl bromides and olefins results in alkanes including linear alkanes and isoalkanes and HBr. The alkanes are discharged from hydrogenation reactor 50 in alkane product stream 54, which may include linear alkanes, isoalkanes and combinations thereof, and the HBr is discharged in hydrogenation HBr stream 56.

In the embodiment shown in FIG. 1, separation system HBr stream 44 and hydrogenation HBr stream 56 are mixed with oxygen, for instance through the introduction of air stream 62 in HBr oxidation system 60. The HBr gas may be oxidized over a catalyst in HBr oxidation system 60, such as a chromium or cerium oxide-based catalyst to produce bromine and water. The initiation temperature for this catalytic reaction is approximately 200° C., while the maximum stable operating temperature for the catalyst is approximately 700° C. HBr oxidation is a highly exothermic reaction and may be carried out using a reactor system, such as an isothermal reactor or a multiple stage adiabatic reactor system with intermediate cooling using quench and/or heat exchangers. Examples of such systems may be found in U.S. Pat. No. 7,883,568, issued Feb. 8, 2011, which is incorporated fully herein by reference.

Wet bromine effluent 64 exits HBr oxidation system 60 and is processed in bromine recovery system 70. In bromine recovery system 70, the bromine in wet bromine effluent 64 may be condensed, and bromine and water (which are substantially immiscible) are separated, such as by using a decanter. Elemental bromine from bromine recovery system 70 may be recycled to bromination reactor 20 through dry bromine stream 72, while water and a gas stream (primarily including nitrogen and oxygen) may be discharged through water discharge stream 74 and gas discharge stream 76, respectively.

Though FIG. 1 depicts the oxidation of HBr with air to produce bromine ($Br_2$), other methods, including electrolysis can also be employed to regenerate $Br_2$ from all or a portion of the HBr generated in the process.

Figure 2:
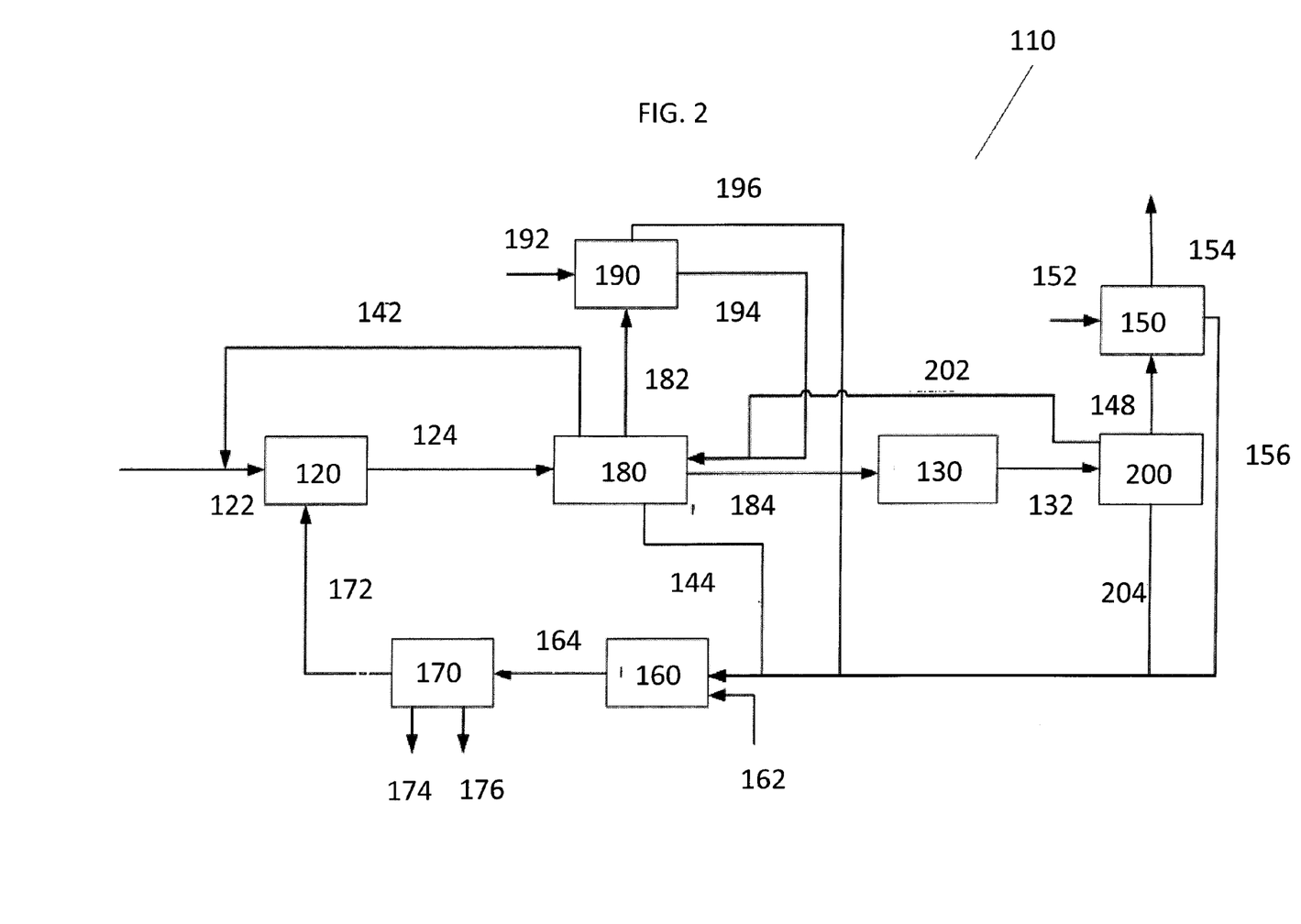
FIG. 2 is a process flow diagram depicting an alkane coupling system consistent with at least one embodiment of the present disclosure.

FIG. 2 is a process flow diagram depicting coupling system 110 consistent with certain embodiments of the present disclosure. In bromination reactor 120, bromination reactor reactants in bromination reactor input stream 122 are reacted with bromine ($Br_2$) from dry bromine stream 172 in a bromination reaction as described with respect to bromination reactor 20 in FIG. 1. The reaction products of the bromine reaction together with unreacted bromination reactor reactants are discharged from bromination reactor 120 through bromination reactor discharge stream 124.

Bromination reactor discharge stream 124 is sent to monoalkylbromide recovery system 180. In monoalkylbromide recovery system 180, the bromination reaction products and unreacted bromination reactor reactants may be separated via distillation and/or absorption/stripping. In certain embodiments, such as shown in FIG. 2, monoalkylbromide recovery system 180 may separate bromination reactor discharge stream 124 into a light hydrocarbon stream 142, which may include the unreacted bromination reactor reactants and olefins having less than the desired number of carbon atoms, as described further with respect to separation system 200; monoalkylbromide recovery HBr stream 144, which includes HBr; alkane polybromides stream 182, which includes polybromoalkanes; and monobromoalkanes stream 184, which includes monobromoalkanes. Light hydrocarbon stream 142 may be recycled to bromination reactor 120 for subsequent bromination.

The polybromoalkanes in alkane polybromides stream 182 are directed to alkyl polybromide reactor 190 and reacted with hydrogen in first hydrogen stream 192. The hydrogenation of the polybromoalkanes in alkyl polybromide reactor 190 may be catalyzed. Non-limiting examples of hydrogenation catalysts include Pd, Pt, Ni, Ru, and Cu. The hydrogenation of the alkyl polybromide reactor 190 results in monbromoalkanes and HBr. Hydrogenation in alkyl polybromide reactor 190 may also result in alkanes, which when separated in monoalkylbromide recovery system 180 would be recycled through light hydrocarbon stream 142. The monobromoalkanes are recycled to monoalkylbromide recovery system 180 in monoalkylbromide recycle stream 194. The HBr is discharged from alkyl polybromide reactor 190 through polybromide reactor HBr stream 196.

The monobromoalkanes in monobromoalkanes stream 184 are directed to coupling reactor 130, where the monobromoalkanes are coupled as described in FIG. 1 with respect to coupling reactor 30. The coupling reactor discharge mixture may be discharged from coupling reactor 130 through coupling reactor effluent 132. Coupling reactor effluent 132 is fed to separation system 200. In separation system 200, the coupling reactor discharge mixture may be separated via distillation and/or absorption/stripping. In certain embodiments, such as shown in FIG. 2, separation system 200 may separate the coupling reactor discharge mixture into monoalkylbromide recovery system recycle stream 202, separation system HBr stream 204, which includes HBr and coupled products stream 148.

Separation system 200 may be adapted to separate hydrocarbons and alkylbromides having less than a desired number of carbon atoms from those with at least the desired number of carbons, as described with respect to separation system 40. Monoalkylbromide recovery system recycle stream 202 may include alkanes, olefins, and alkyl bromides having less than the desired number of carbon atoms. Monoalkylbromide recovery system recycle stream 202 may be recycled to monoalkylbromide recovery system 180 for further separation. Coupled products stream 148 may include olefins, alkyl bromides and alkanes having at least the desired number of carbon atoms.

Coupled products stream 148 is hydrogenated with $H_2$ stream 152 in hydrogenation reactor 150 as described with respect to hydrogenation reactor 50 in FIG. 1. The alkanes are discharged from hydrogenation reactor 150 in alkane product stream 154, which includes linear alkanes and isoalkanes, and HBr, which is discharged through hydrogenation HBr stream 156.

The HBr in monoalkylbromide recovery HBr stream 144, separation system HBr stream 204, polybromide reactor HBr stream 196, and hydrogenation HBr stream 156 are mixed with oxygen, for instance through the introduction of air stream 162 in HBr oxidation system 160, and oxidized as described with respect to HBr oxidation system 60 in FIG. 1. The resulting wet bromine effluent 164 exits HBr oxidation system 160 and is processed in bromine recovery system 170 as described with respect to bromine recovery system 70 in FIG. 1. Elemental bromine from bromine recovery system 170 may be recycled to bromination reactor 120 through dry bromine stream 172, while water and a gas stream (primarily including nitrogen and oxygen) may be discharged through water discharge stream 174 and gas discharge stream 176, respectively.

In another embodiment, ethane is incorporated into the product alkanes. As both carbon atoms in ethane are primary, the bromination of ethane may require higher temperatures than that required for brominating $C_3$ to $C_{10}$ alkanes. In certain circumstances, when a stream of $C_2$ to $C_{10}$ alkanes is mixed with bromine at a temperature sufficient to brominate ethane, the resulting product may contain undesirable concentrations of polybrominated $C_3$ to $C_5$ alkanes and/or low levels of ethane conversion.

Figure 3:
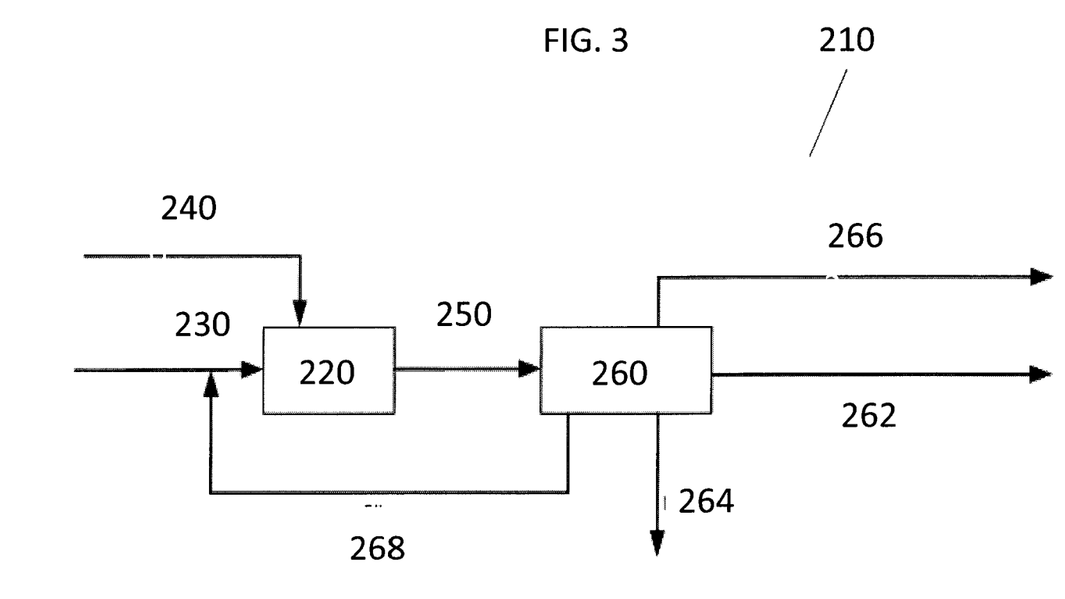
FIG. 3 is a process flow diagram depicting an ethane bromination system consistent with at least one embodiment of the present disclosure.

FIG. 3 depicts an embodiment of ethane bromination system 210 for generating a brominated ethane stream for incorporation into an oligomerized alkane. In ethane bromination reactor 220, ethane in ethane feed stream 230 is reacted with bromine ($Br_2$) in bromine feed stream 240 to produce ethyl bromides and HBr. Reaction conditions in ethane bromination reactor 220 (reactant ratios, temperature, pressure and residence time) are selected so as to maximize the yield of monobromoethane, minimize formation of polybromoethane, and ensure complete conversion of bromine. For instance, ethane bromination reactor 220 may operate at a temperature of between 300 and 550° C. or between 375 and 450° C., at a pressure of between 0.5 and 50 atmospheres or between 5 and 35 atmospheres, and with a residence time of between 1 and 60 seconds or between 5 and 30 seconds. The ethyl bromides and HBr exit ethane bromination reactor 220 through ethane bromination reactor discharge 250 and are separated into four streams in ethane ethyl bromide recovery system 260 via distillation and/or absorption/stripping: monobromoethane stream 262, polybromoethane stream 264, HBr stream 266, and unreacted ethane stream 268. The ethane in unreacted ethane stream 268 is recycled to ethane bromination reactor 220. The remaining streams (monobromoethane stream 262, polybromoethane stream 264, and HBr stream 266) may be combined with process streams as described with respect to FIG. 2. The ethyl bromide in monobromoethane stream 262 may be combined with monobromoalkanes stream 184 and directed to coupling reactor 130 for coupling. The polybromoethane in polybromoethane stream 264 may be combined with alkane polybromides stream 182, directed to alkyl polybromide reactor 190 and reacted with hydrogen in first hydrogen stream 192. The HBr in HBr stream 266 may be directed to HBr oxidation system 160.

The above examples demonstrate possible embodiments of the present disclosure. While the foregoing is directed to embodiments, versions and examples, which are included to enable a person of ordinary skill in the art to make and use the embodiments when the information in this patent is combined with available information and technology, the disclosure is not limited to only these particular embodiments, versions and examples. Other and further embodiments, versions and examples may be devised without departing from the basic scope thereof and the scope thereof is determined by the claims that follow.

What is claimed is:

1. A method comprising:
    reacting a stream comprising one or more C3 to C10 alkanes and less than 2% ethane and 1% methane with bromine in a bromination reactor to form a bromination reactor discharge stream comprising alkylbromides and HBr;
    separating the discharge stream into an alkylbromide stream and a first HBr stream in a monobromoalkyl recovery system;
    sending the alkylbromide stream to a coupling reactor to form a coupling reactor effluent comprising alkylbromides having between 5 and about 1000 carbon atoms, olefins having between 5 and about 1000 carbon atoms and HBr;
    separating the coupling reactor effluent into a second HBr stream, a heavy alkylbromide stream, a light alkylbromide stream, a heavy olefin stream, and a light olefin stream, wherein the heavy alkylbromide stream and heavy olefin stream comprise heavy alkylbromides having at least 8 carbon atoms heavy olefins having at least 8 carbon atoms and the light alkylbromide stream and light olefin stream comprise light alkylbromides having less than 8 carbon atoms and light olefins having less than 8 carbon atoms;
    recycling the light olefins to the bromination reactor;
    recycling the light alkylbromides to the coupling reactor; and
    hydrogenating the heavy alkylbromides and heavy olefins to form C8+ alkanes and HBr.

2. The method of claim 1, wherein the one or more $C_3$ to $C_{10}$ alkanes are one or more $C_3$ to $C_5$ alkanes.

3. The method of claim 1, wherein the temperature of the bromination reactor is between 200° C. and 375° C.

4. The method of claim 1, wherein the temperature of the coupling reactor is between 180° C. and 300° C.

5. The method of claim 1, wherein the pressure of the coupling reactor is between 2 and 100 atmospheres.

6. The method of claim 1, wherein the residence time of the alkylbromides in the coupling reactor is between about 1 second and about 45 seconds.

7. The method of claim 1, wherein the heavy alkylbromide stream and the heavy olefin stream comprise heavy alkylbromides having at least 10 carbon atoms and heavy olefins having at least 10 carbon atoms.

8. The method of claim 1, further comprising:
oxidizing the first HBr stream and the second HBr stream with oxygen in an HBr oxidation reactor to form a wet bromine stream comprising water and bromine;
separating the water from the bromine in a bromine recovery system; and
recycling the bromine to the bromination reactor.

9. The method of claim 1, further comprising prior to the step of coupling:
further separating the bromination reactor discharge stream into:
a light hydrocarbons stream comprising the unreacted $C_3$ to $C_{10}$ alkanes;
an alkane polybromides stream comprising polybromoalkanes; and
a monobromoalkanes stream comprising monobromoalkanes;
hydrogenating the alkane polybromides stream to form a polybromide reactor HBr stream comprising HBr and a monoalkylbromide recycle stream comprising monobromoalkanes, wherein the monoalkylbromide recycle stream is recycled to the monobromoalkyl recovery system; and
feeding the monobromoalkanes stream to the coupling reactor.

10. The method of claim 9, further comprising:
oxidizing the first HBr stream, the second HBr stream, and the polybromide reactor HBr stream with oxygen in an HBr oxidation reactor to form a wet bromine stream comprising water and bromine;
separating the water from the bromine in a bromine recovery system; and
recycling the bromine to the bromination reactor.

11. A method comprising:
reacting ethane with bromine in an ethane bromination reactor to form an ethane bromination reactor discharge comprising monobromoethane, polybromoethane, HBr and ethane;
separating the ethane bromination reactor discharge to form a monobromoethane stream, a polybromoethane stream, an ethane bromination HBr stream, and an unreacted ethane stream;
recycling the unreacted ethane stream to the ethane bromination reactor;
reacting a stream comprising one or more $C_3$ to $C_{10}$ alkanes and less than 2% ethane and 1% methane with bromine in a bromination reactor to form a bromination reactor discharge stream comprising alkylbromides, unreacted $C_3$ to $C_{10}$ alkanes and HBr;
separating the bromination reactor discharge stream in a monobromoalkyl recovery system into:
a light hydrocarbons stream comprising the unreacted $C_3$ to $C_{10}$ alkanes;
a monoalkylbromide recovery HBr stream comprising HBr;
an alkane polybromides stream comprising polybromoalkanes; and
a monobromoalkanes stream comprising monobromoalkanes;
combining the monobromoethane stream with the monobromoalkanes stream;
combining the polybromoethane stream with the alkane polybromides stream;
hydrogenating the polybromoalkanes in the alkane polybromides stream to form a polybromide reactor HBr stream comprising HBr and a monoalkylbromide recycle stream comprising monobromoalkanes, wherein the monoalkylbromide recycle stream is recycled to the monobromoalkyl recovery system;
feeding the monobromoalkanes stream to a coupling reactor;
coupling the monobromoalkanes in the coupling reactor to form a coupling reactor effluent comprising alkylbromides having between 5 and about 1000 carbon atoms, olefins between 5 and about 1000 carbon atoms and HBr; and
hydrogenating the alkylbromides having between 5 and about 1000 carbon atoms and olefins having between 5 and about 1000 carbon atoms to form alkanes having between 5 and about 1000 carbon atoms and HBr.

12. The method of claim 11, further comprising after the step of coupling the monobromoalkanes in the coupling reactor:
separating the coupling reactor effluent into:
a separation system HBr stream comprising HBr;
a heavy alkylbromide stream;
a light alkylbromide stream;
a heavy olefin stream; and
a light olefin stream;
wherein the heavy alkylbromide stream and heavy olefin stream comprise at least 8 carbon atoms and the light alkylbromide stream and light olefin stream comprise less than 8 carbon atoms;
recycling the light alkylbromide stream and the light olefin stream to the monobromoalkyl recovery system; and
wherein the step of hydrogenating is performed on the heavy alkylbromides and the heavy olefins.

13. The method of claim 12, further comprising:
oxidizing the ethane bromination HBr stream, the monoalkylbromide recovery HBr stream, the polybromide reactor HBr stream, and the separation system HBr stream with oxygen in an HBr oxidation reactor to form a wet bromine stream comprising water and bromine;
separating the water from the bromine in a bromine recovery system; and
recycling the bromine to the bromination reactor.

14. The method of claim 12, wherein the heavy alkylbromide stream and the heavy olefin stream comprise at least 10 carbon atoms, and the alkanes formed by the hydrogenation step are C10+ alkanes.

15. The method of claim 11, wherein the temperature in the ethane bromination reactor is between 300° C. and 550° C.

16. The method of claim 11, wherein the pressure of the ethane bromination reactor is between 5 and 35 atmospheres.

17. The method of claim 11, wherein the temperature in the bromination reactor is between 200° C. and 450° C.

18. The method of claim 11, wherein the temperature in the coupling reactor is between 180° C. and 300° C.

* * * * *